US010939867B2

(12) United States Patent
Bray, Jr.

(10) Patent No.: US 10,939,867 B2
(45) Date of Patent: Mar. 9, 2021

(54) PARALYSIS MONITORING SYSTEM

(71) Applicant: Robert S. Bray, Jr., Marina Del Ray, CA (US)

(72) Inventor: Robert S. Bray, Jr., Marina Del Ray, CA (US)

(73) Assignee: Robert S. Bray, Marina Del Rey, CA (US)

(*) Notice: Subject to any disclaimer, the term of this patent is extended or adjusted under 35 U.S.C. 154(b) by 355 days.

(21) Appl. No.: 15/914,574

(22) Filed: Mar. 7, 2018

(65) Prior Publication Data
US 2018/0256097 A1 Sep. 13, 2018

Related U.S. Application Data

(60) Provisional application No. 62/469,797, filed on Mar. 10, 2017.

(51) Int. Cl.
*A61B 5/00* (2006.01)
*A61B 5/0492* (2006.01)
(Continued)

(52) U.S. Cl.
CPC .......... *A61B 5/4821* (2013.01); *A61B 5/0492* (2013.01); *A61B 5/4519* (2013.01); *A61B 5/4839* (2013.01); *A61B 5/6848* (2013.01); *A61N 1/0452* (2013.01); *A61N 1/36003* (2013.01); *A61B 2505/05* (2013.01); *A61B 2560/0475* (2013.01)

(58) Field of Classification Search
CPC ... A61B 5/4821; A61B 5/4519; A61B 5/4839; A61N 1/00; A61N 1/18; A61N 1/32; A61N 1/36; A61N 1/0452; A61N 1/36003
See application file for complete search history.

(56) References Cited

U.S. PATENT DOCUMENTS 2,979,055 A 4/1961 De Beer et al.
4,893,630 A 1/1990 Bray, Jr.
(Continued)

FOREIGN PATENT DOCUMENTS

EP 3592228 A1 1/2020
WO 2005028029 A2 3/2005
WO 2018165402 A1 9/2018

OTHER PUBLICATIONS

International Preliminary Report on Patentability dated Sep. 19, 201 for International Application No. PCT/US2018/021501.
(Continued)

*Primary Examiner* — Daniel L Cerioni
*Assistant Examiner* — Raymond P Dulman
(74) *Attorney, Agent, or Firm* — Plumsea Law Group, LLC

(57) ABSTRACT

A paralysis monitoring system can be utilized during various medical procedures. Generally, the system is used during procedures involving anesthesia, when general paralysis is necessary, e.g., during surgery that requires cutting through or mobilizing muscle tissue. The paralysis monitoring system stimulates a nerve with low voltage signals and can provide for continuous monitoring and recording of the evoked muscle activity throughout and after a procedure. By monitoring a quantitative response of the muscle activity to nerve stimulation, an anesthesiologist may adjust subsequent doses of a paralytic agent to achieve a desired level of paralysis.

20 Claims, 13 Drawing Sheets

(51) Int. Cl.
*A61N 1/04* (2006.01)
*A61N 1/36* (2006.01)

(56) References Cited

U.S. PATENT DOCUMENTS

| | | | |
|---|---|---|---|
| 6,016,449 A | 1/2000 | Fischell et al. | |
| 6,016,499 A | 1/2000 | Fischell et al. | |
| 6,146,335 A | 11/2000 | Gozani | |
| 6,233,472 B1 | 5/2001 | Bennett et al. | |
| 6,325,764 B1 | 12/2001 | Griffith et al. | |
| 6,507,755 B1 | 1/2003 | Gozani et al. | |
| 6,685,649 B2 | 2/2004 | Korhonen | |
| 8,439,836 B2 | 5/2013 | Storm | |
| 8,989,866 B2 | 3/2015 | Gharib et al. | |
| 9,084,550 B1 | 7/2015 | Bartol et al. | |
| 2004/0243017 A1 | 12/2004 | Causevic | |
| 2005/0085741 A1 | 4/2005 | Hoskonen et al. | |
| 2007/0167859 A1* | 7/2007 | Finneran | A61B 5/0492 600/546 |
| 2008/0243021 A1 | 10/2008 | Causevic et al. | |
| 2009/0177112 A1 | 7/2009 | Gharib et al. | |
| 2011/0137297 A1* | 6/2011 | Kiani | A61B 5/0402 604/890.1 |
| 2012/0245482 A1 | 9/2012 | Bolser et al. | |
| 2012/0259239 A1 | 10/2012 | Chenaux et al. | |
| 2013/0184779 A1* | 7/2013 | Bikson | A61N 1/36034 607/45 |
| 2013/0204155 A1* | 8/2013 | Brull | A61B 5/1106 600/546 |
| 2013/0331711 A1 | 12/2013 | Mathur et al. | |
| 2014/0018695 A1 | 1/2014 | Farquhar | |
| 2014/0163412 A1 | 6/2014 | Jacobson et al. | |
| 2014/0236142 A1* | 8/2014 | Ward | A61B 18/1233 606/38 |
| 2016/0045746 A1 | 2/2016 | Jiang et al. | |
| 2016/0157753 A1 | 6/2016 | Sternberger | |

OTHER PUBLICATIONS

International Search Report and Written Opinion dated Jul. 27, 2018 for International Application No. PCT/US2018/021501.
First examination report dated Dec. 6, 2019 for Australian Patent Application No. 2018231042.
Saenz, Agustina D. "Peripheral Nerve Stimulator—Train of Four Monitoring" Sep. 16, 2015; retrieved from Internet Jun. 11, 2018 <http://emedicine.medscape.com/article/2009530-overview#a1>.
Invitation to Pay Additional Fees and, Where Applicable, Protest Fee issued on Jun. 8, 2018 for International Application No. PCT/US2018/21501.
Second examination report dated Jun. 16, 2020 for Australian Patent Application No. 2018231042.
Extended European Search Report dated Nov. 19, 2020 for European Patent Application No. EP18764372.1.
Ritchie G. et al., "A Microcomputer Based Controller for Neuromusucular Block During Surgery", Annals of Biomedical Engineering, Springer US, New York, vol. 13, No. 1, published Jan. 1, 1985, pp. 3-15, XP000607570, ISSN: 0090-6964.

* cited by examiner

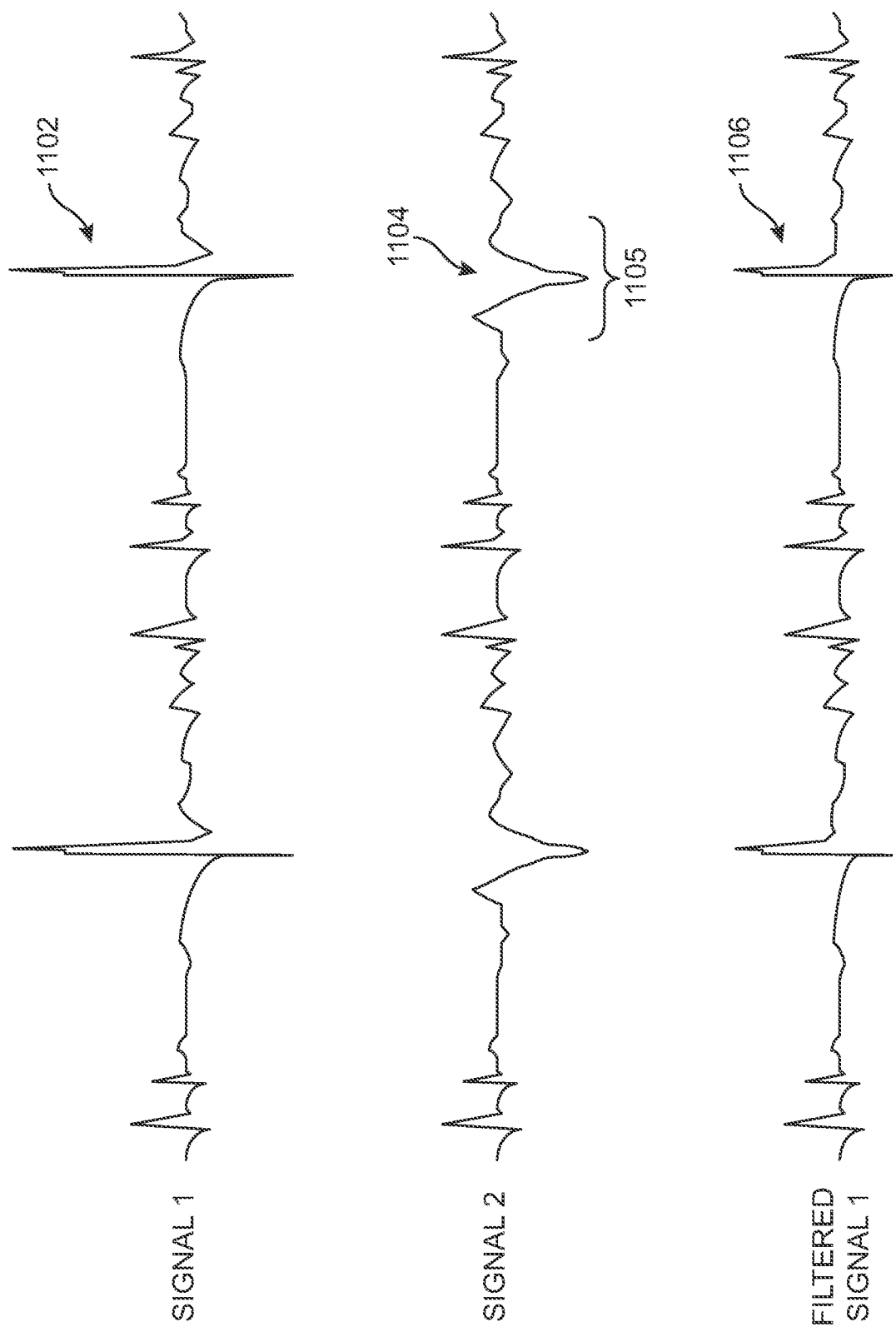

PARALYSIS MONITORING SYSTEM

RELATED APPLICATIONS

This application claims priority to U.S. Provisional Patent Application No. 62/469,797, to Bray, filed Mar. 10, 2017, and titled "Paralysis Monitoring System," the entirety of which is herein incorporated by reference.

BACKGROUND

Paralysis monitoring systems can be utilized during various medical procedures. Generally, these systems are used during procedures involving anesthesia, when general paralysis is necessary, e.g., during surgery that requires access through muscle tissue. During such procedures, healthcare professionals (such as physicians, anesthesiologists, doctors, surgeons, technicians, and other health-related personnel) generally utilize different techniques that can indicate to some extent the level of paralysis of a patient. In some cases, physicians have typically utilized a stimulating probe with visual documentation of muscle contraction, which is conventionally referred to as a "train-of-four." This type of conventional neuromuscular monitoring is used during the application of general anesthesia with paralysis to determine approximately how well a patient's muscles are able to function. The conventional train-of-four monitoring technique is applied intermittently. The conventional technique uses four stimulating electrical impulses of approximately 20 mV that are placed over the nerve in a superficial area, such as the face, elbow, ulnar nerve or peroneal nerve in the leg. During the conventional train-of-four monitoring, the physician looks for gross motor motions of the patient to ascertain that the level of paralysis administered to the patient with a long-acting depolarizing agent is adequate, indicating a loss of muscle activity, as well as for signs that activity has begun to return so that anesthesia may be terminated. When a patient is under paralysis there is a loss of the train-of-four responses.

The conventional train-of-four monitoring technique involves stimulation of the nerve and contemporaneous visual observation and documentation of spasms or reactions of the muscle. As paralysis or paralytic agents—such as curare derivative agents or nondepolarizing agents—are administered, a neuromuscular blockade of a patient's muscle activity can occur. The train-of-four technique is typically used after the administration of the paralysis agent to document that the ability to move has been lost and the patient is now "paralyzed". The technique is also used at the end of a procedure to demonstrate a return of the train-of-four responses, such that a patient may be extubated from anesthesia.

As will be described below, there are several drawbacks to the use of the conventional 'train-of-four' technique. It is understood that the train-of-four tests cannot be repeated more than a few times because of the high stimulus used, which can create a burning effect of the nerve, numbness, tingling and painful dysesthesias of the nerve. Thus, this conventional technique cannot be used as a continuous monitoring device. Further, prior to a surgical procedure, patients are typically preloaded with a heavy dose of a paralytic agent, which is allowed to wear off over time. However, the dosage and administration of the drug may be associated with highly variable responses as its metabolism varies from one patient to another patient. Thus, train-of-four neuromuscular monitoring can be quite inaccurate in ascertaining whether complete paralysis has occurred or reversed. In some cases, during a procedure, there will be a loss of the train-of-four impulse recordings although the patient has not yet reached a state of complete paralysis. In addition, because the length of time and metabolism of the drug is quite variable, there can be situations where inadequate paralysis is obtained during the procedure. There can also be difficulty maintaining muscle retraction, and there may be other significant problems, such as increased bleeding and loss of exposure, when muscle retraction returns.

Furthermore, if paralysis remains present when the procedure is completed and the anesthesia is allowed to wear off or lighten over time, there is the risk that a patient may awaken or regain consciousness while still in a state of paralysis. In other words, the patient can go through a period where he or she is too weak to breathe, and/or unable to move. This can be a highly distressful or panic-evoking experience for the patient. A reversal agent for the paralysis drug can be given to the patient, but these drugs have other shortcomings. For example, reversal agents are typically short-acting, and generally administered at the end of a procedure. The patient would begin to experience a decrease in paralysis and wake up and move, but within approximately 20-30 minutes the effects of the reversal agent can wear off. If the paralysis agent has not been fully metabolized, the patient will automatically re-paralyze at this point, which can lead to respiratory dysfunction or even death. This has been documented in post-anesthesia cases if the patient is unobserved during this period. Additional doses of a reversal agent cannot be given as they have a paradoxical effect of recreating paralysis because the metabolism time and dosing are very variable. Thus, it is very difficult for an anesthesiologist to determine the proper dose for each individual. Furthermore, there is reluctance to increase the dosage of the paralysis agent during the middle or end of the procedure case for fear that it will not wear off and there will be difficulties awakening the patient under paralysis.

As described, prior or conventional paralysis monitoring techniques used in this area of medicine can only be used very intermittently, and are inaccurate in determining the level of paralysis. Such systems do not allow continuous monitoring that is critical to determining the level of paralysis under anesthesia. In addition, these systems cannot be used in conscious patients due to the level of pain that can be caused.

SUMMARY OF THE INVENTION

In one aspect, a paralysis monitoring system includes a nerve stimulation device configured to deliver a series of low voltage electrical impulses to a nerve to produce only sub-visible muscle responses, and a recording device configured to record electrical activity associated with an evoked muscle response caused by the series of low voltage electrical impulses.

In another aspect, a paralysis monitoring system includes a nerve stimulation device configured to deliver a series of low voltage electrical impulses to a nerve, a first recording device configured to record electrical activity associated with an evoked muscle response to the nerve stimulation device, and a second recording device configured to record electrical activity associated with the series of low voltage electrical impulses to the nerve. The first recording device is configured to be placed over a target muscle group associated with the nerve and the second recording device is configured to be disposed away from the target muscle group.

In another aspect, a method of administering a paralysis drug includes attaching a stimulation device to a patient's anatomy, attaching a recording device to the patient's anatomy and administering a first dose of a paralysis agent to the patient. Following this, the method includes transmitting low voltage electrical impulses from the stimulation device to the patient, receiving a response signal corresponding to muscle activity of the patient in the recording device and using information related to the response signal to determine an amount of the paralysis agent to administer as a second dose. Then the second dose of the paralysis agent may be delivered to the patient.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

FIG. 13 is a schematic view of several different electrical signals, according to an embodiment.

DETAILED DESCRIPTION

Figure 1:
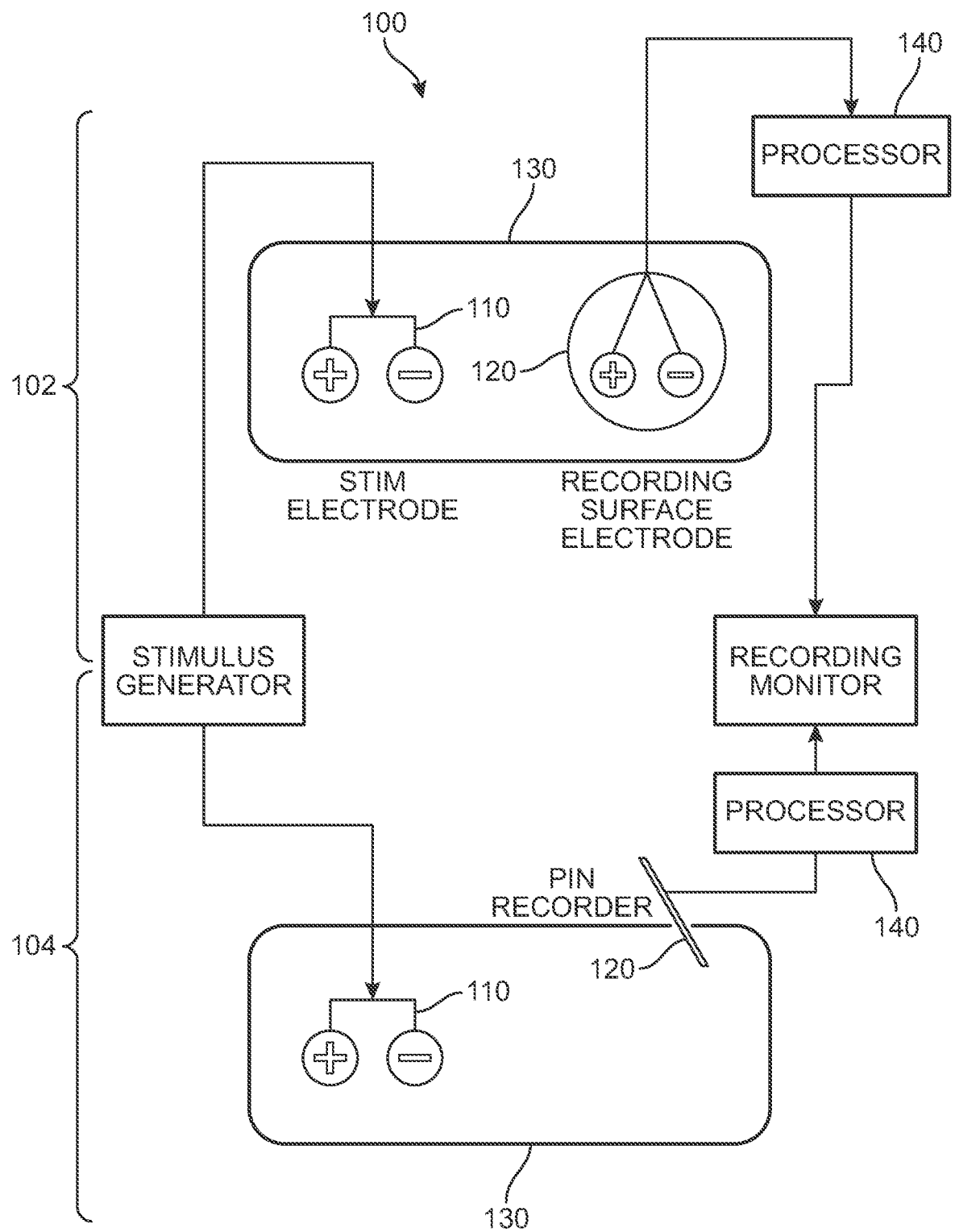
FIG. 1 is a schematic view of two embodiments of components of a paralysis monitoring system constructed according to the principles of the invention.

There is a need for a monitoring system that can reliably provide information pertaining to the neuromuscular condition of the patient before, during, and after a procedure. Current techniques do not permit medical professionals to accurately ascertain whether a patient remains paralyzed throughout the entirety of a procedure. During a surgical procedure—in particular during major procedures which can run several hours—the safety of the patient becomes an increasingly difficult challenge. The determination of the point at which it is safe to extubate the patient and/or the risk of employing too much paralysis agent are only some issues that can cause problems in recovery, leading to situations where a patient is too weak to breathe. A monitoring system that overcomes these problems would provide healthcare professionals with a formidable lifesaving alternative.

The embodiments may avoid one or more of the drawbacks with the conventional train-of-four monitoring approach and may meet one or more of the foregoing needs by providing a paralysis monitoring system that allows for continuous monitoring of (a) the depth of paralysis present, (b) the level of reversibility of the patient, and/or (c) a safety margin for extubation.

In addition, the exemplary embodiments of the invention include provisions for stimulation of nerves and uses $\frac{1}{10}$ to $\frac{1}{100}$ of the current compared to the conventional train-of-four method, and may record an evoked response from a muscle in the corresponding distribution of the stimulated nerve. The nerve can be stimulated transcutaneously in some embodiments, the evoked muscle response can be recorded via either a small pin or a surface patch (Electromyogram, referred to as EMG), or a classic pin that is in contact with the distributed muscles from the stimulated nerve or the muscle/nerve interface. In contrast to the conventional train-of-four method, which can only be applied 3-4 times and relies upon an observed response, embodiments of the invention allow for repeated stimulations, due to the administration of a current that ranges from $\frac{1}{10}$-$\frac{1}{100}$ relative to the current used by the conventional train-of-four method. As an example, where the conventional train-of-four method might administer a stimulating current of 20-40 mA to a patient, embodiments of the invention might only apply a current in a range between 0.2 mA-4 mA. It should be understood that these numbers are provided for comparison purposes only, and in other cases, the amount of current that is administered using the inventive concepts could vary. It may be appreciated that the embodiments may use low voltages along with low currents and in some cases the voltages could be substantially lower than the voltages applied during conventional train-of-four techniques.

In addition, in some embodiments muscle activity can be filtered out from the recording as noise while the evoked muscle response is recorded. Thus, rather than rely upon visual observations of a muscle response, embodiments of the invention may record a graded return response of evoked muscle activity. Furthermore, embodiments employing the inventive concepts may provide a continuous monitoring technique in the postoperative period.

Some of the advantages of the invention include a dramatic decrease in the risks associated with paralysis during procedures requiring anesthesia, simplification of the processes of monitoring paralysis and/or administrating paralysis agents in precise, measured amounts tailored to the individual patient's need. In addition, embodiments of the invention avoid reliance on conventional, crude visual observations of muscle responses, and automatically accounts for the variability of patient physical characteristics such as skin thickness, temperature of the patient's extremities, etc., with a reliable neuromuscular recording.

As shown in FIG. 1, in different embodiments, a paralysis monitoring system ("monitoring system") 100 can be utilized during various medical procedures involving anesthesia when general paralysis is administered. Monitoring system 100 is capable of continuously monitoring the depth of paralysis of a patient before, during and after the procedure requiring paralysis. Moreover, information obtained from monitoring system 100 may be used when determining the quantity of a paralytic agent to be administered at different points during a procedure.

Figure 8:
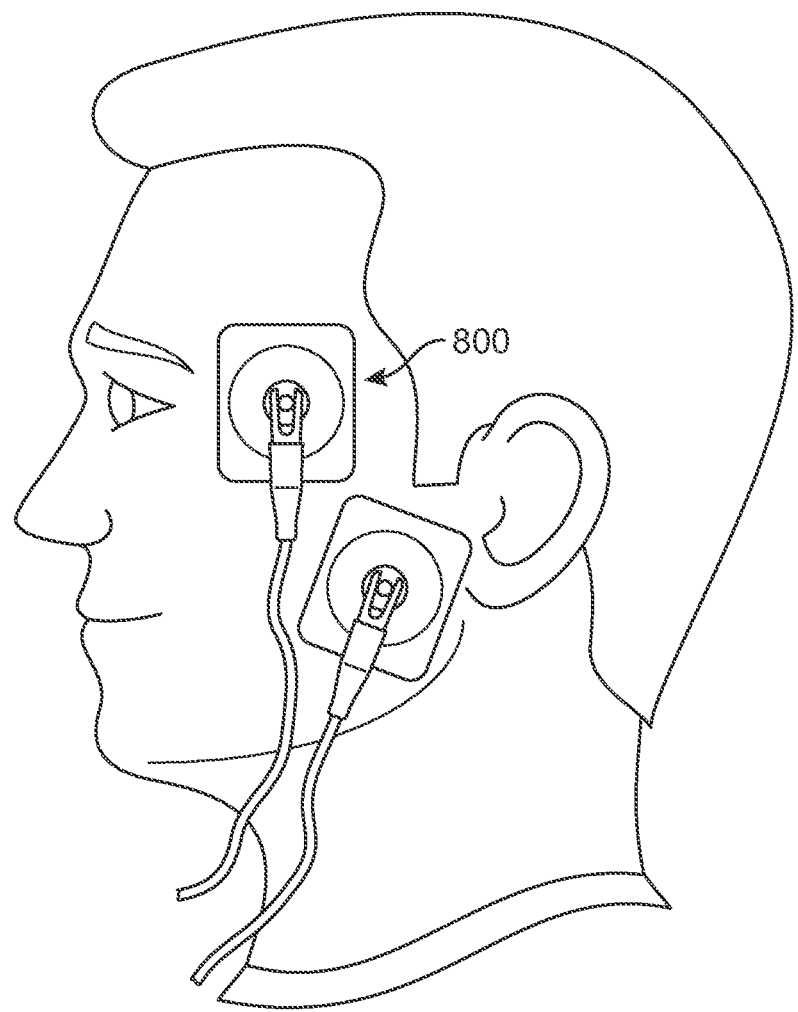
FIG. 8 is a schematic view of placement of surface electrodes over the facial nerve for stimulating a nerve according to the principles of the embodiments.

Monitoring system 100 can include different components. FIG. 1 depicts two different embodiments of monitoring system 100, denoted as a first system 102 and a second system 104. In both first system 102 and second system 104, the monitoring system includes a stimulation electrode device 110 and a recording device 120. The stimulation electrode device may be in the form of a pair of surface electrodes 800, as shown in FIG. 8, or a bipolar stimulating probe, or another suitable stimulating device. The recording device may be in the form of a recording surface electrode or a pin recorder as shown in FIG. 1. First system 102 and second system 104 are shown together for illustrative purposes and it should be understood that monitoring system 100 can comprise only one stimulation electrode device and one recording device in some embodiments. Furthermore, the type of stimulation electrode device and/or recording device utilized in monitoring system 100 can vary in different embodiments, as will be discussed below.

In different embodiments, stimulation electrode device 110 can comprise a transcutaneous skin stimulus with variable probe with electrodes or any other device capable of safely delivering milliamp pulses to humans at varying intensities. In some embodiments, monitoring system 100 is a constant monitoring device that provides a single impulse to the nerves of a patient. The single impulse is read as a percentage of the baseline monitoring (further detail regarding the baseline recording will be discussed below).

A stimulation device is configured to deliver a low voltage (and low current) electrical signal to a region of tissue adjacent a nerve. It may be appreciated that different levels of voltage can have different effects on a target muscle (that is, the muscle associated with the targeted nerve). For systems relying on a visual (or motion based) muscle response, the level of voltage generated by a stimulating apparatus must be sufficient to contract the muscle to the point where a muscle twitch, or visual muscle contraction is observable. It may be appreciated, however, that lower voltages could be applied to evoke a response in a target muscle that is not directly observable with the eye or other motion sensitive devices (e.g., accelerometers). For example, sufficiently low voltages might generate a "sub-visible response." A sub-visible response may include a sub-visible contraction or a sub-visible twitch that cannot be detected by a visual observation of the patient anatomy. During a sub-visible response, muscle fibers may contract but the contraction may be insufficient (or the number of fibers firing simultaneously is too few) to cause any substantial movement that could be visually detected. However, though the muscle may not move/twitch, electrical signals generated by the muscle in response to the stimulation voltage may still be detectable by a recording device capable of sensing electrical signals (e.g., surface electrodes or subcutaneous probes). By using recording devices that detect electrical signals directly from the muscle, the embodiments provide a system that can make use of very low voltages compared to systems that rely on visual or motion-based detection. Therefore, the embodiments may include systems and methods for generating a voltage that is insufficient to cause a visible muscle response (e.g., visible contraction or twitch) and also of providing recording devices capable of detecting sub-visible muscle responses. Put another way, the embodiments use a stimulation device to generate low voltage signals that produce only sub-visible responses in a muscle and use a recording device capable of detecting the sub-visible responses.

In different embodiments, the range of voltages generated by a stimulation device during monitoring could vary. In some embodiments, the voltage could have any value approximately in a range between 0.1 and 4 millivolts. In some embodiments, the range of voltages applied could vary according to factors including the size and weight of the patient. For example, in some embodiments, the range of voltages applied may be approximately between 0.5 and 1.5 millivolts for patients having a body mass index in a first range and the range of voltages applied may be approximately between 1.5 and 4 millivolts for patients having a body mass index in a second range that is higher than the first range. It may be appreciated that body mass index is only one example of a parameter that may be used to help determine an appropriate range of low voltage signals to be applied by a stimulation device.

Because the monitoring system is configured to detect sub-visible muscle responses, it may be more sensitive to subtle changes in muscle response than systems that rely on visually observable, or motion based, responses. This allows the muscle responses to be more readily quantified so that the level of paralysis can be precisely determined. Moreover, the precision obtained using the exemplary system can be greater than the precision obtained using more conventional techniques (e.g., train-of-four) that are insensitive to any changes in muscle response that might occur at the sub-visible level.

In some embodiments, recording device 120 may comprise any device known in the art that can determine, evaluate, or measure the degree of electrical activity of muscle cells, including invasive and non-invasive electrodes. Non-invasive electrodes, or surface electrodes, assess muscle functioning by recording evoked muscle responses from the skin surface (above the muscle). Surface electrodes are secured on the skin and are able to provide an assessment of the evoked muscle responses below. While a surface electrode is placed over the muscle on the skin, with invasive electrodes, a needle electrode is inserted through the skin into the muscle to record the electrical activity of that muscle. Needle electrodes assess voluntary motor activity as can be done with surface electrodes, as well as 'insertional' activity which occurs when the needle is inserted into the muscle.

In some embodiments, monitoring system 100 further comprises an automated machine, including a disposable apparatus with both the stimulating probe and recording probe. Furthermore, in some embodiments, monitoring system 100 is configured to produce an output that is standard and can plug into any given anesthesia machine to allow for continuous monitoring throughout the case.

In some embodiments, recording device 120 may be configured to continuously monitor the electrical activity in a muscle of a human being in response to a low voltage electrical stimulus applied by stimulation electrode device 110. For example, recording device 120 can record spike discharges produced by the stimulated muscle, which is seen as a "spike focus." The spike focus is normally a function of time and is describable in terms of its amplitude, frequency and phase, measuring electrical currents generated in muscles during its contraction which represent neuromuscular activities.

Thus, in one embodiment, recording device 120 may comprise surface electrodes (as shown in first system 102) or needle electrodes (as shown in second system 104). In other words, recording device 120 can be applied to the surface of the skin or can include a type of pin that is inserted into the skin. For example, with a needle EMG, a needle electrode may be inserted directly into a nerve to record the electrical activity associated with a particular muscle. It should be understood that the recording device is generally disposed on a patient's anatomy in such a location so as to correspond to or allow recording of the electrical activity of the muscle that is being stimulated by the stimulation device.

In other embodiments, monitoring system 100 can include an optional connecting device that allows stimulation electrode device 110 and recording device 120 to be readily manipulated in concert, and be correctly positioned on a patient. For example, as shown in FIG. 1, monitoring system 100 includes a strip 130. In some embodiments, strip 130 may include a disposable material, where monitoring system 100 is a one-time use system, facilitating the hygienic utilization of monitoring system 100. However, in other embodiments, strip 130 is a reusable portion of material that can be easily cleaned and used during multiple procedures. Furthermore, in some embodiments, strip 130 may include an adhesive to allow for the easy application of monitoring system 100. In one embodiment, strip 130 can be an elongated material designed for ready and comfortable application and/or removal from a patient's anatomy.

Figure 9:
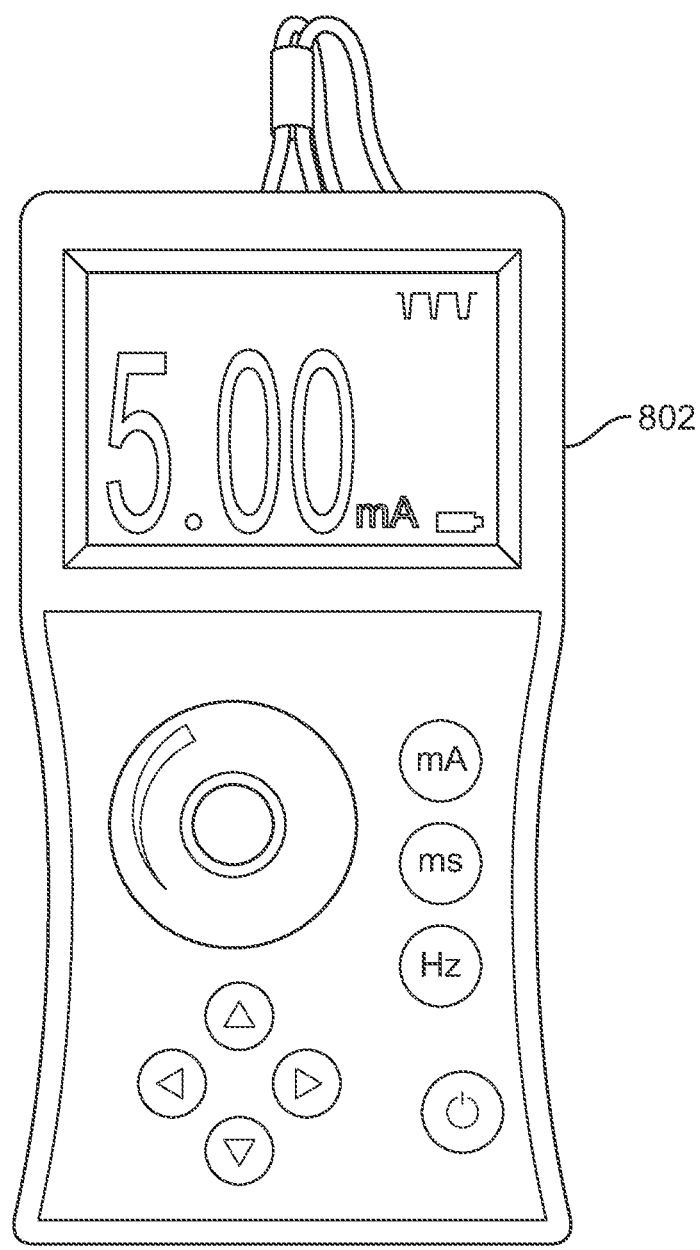
FIG. 9 is a schematic view depicting a type of stimulus generator that may be used to generate millivolt signals to be applied to a nerve according to the principles of the embodiments.
Figure 10:
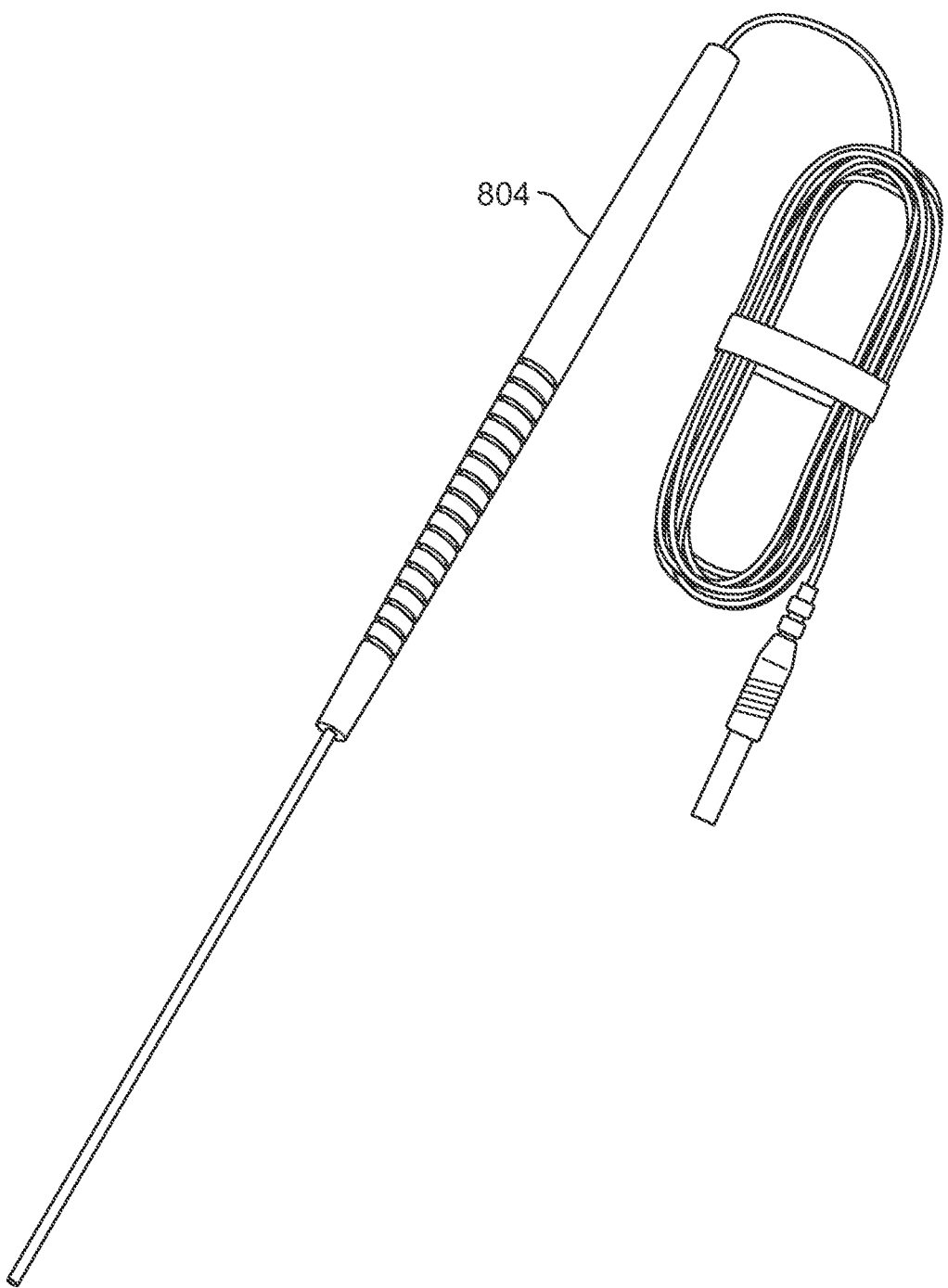
FIG. 10 is a schematic view of a type of monopolar point impulse generator that may be used to stimulate a nerve according to the principles of the embodiments.

Furthermore, in some embodiments, monitoring system 100 can comprise a computer processing unit ("processing unit") 140, which contains suitable processing and memory components to carry out the sensing and recording functions of the system. Though in some embodiments processing unit 140 can be part of or integrated into recording device 120, in other embodiments processing unit 140 may comprise an independent component of monitoring system 100. In different embodiments, processing unit 140 can be configured with an analysis board, which can connect or link to a paralysis agent delivery device ("paralysis agent device") or an anesthesia delivery machine, and/or may provide a means of communicating information between different devices. Thus, in some embodiments, monitoring system 100 can be configured with an output means that facilitates an easy connection or plug-in to standard anesthesia delivery machines (see FIGS. 9 and 10).

Figure 2:
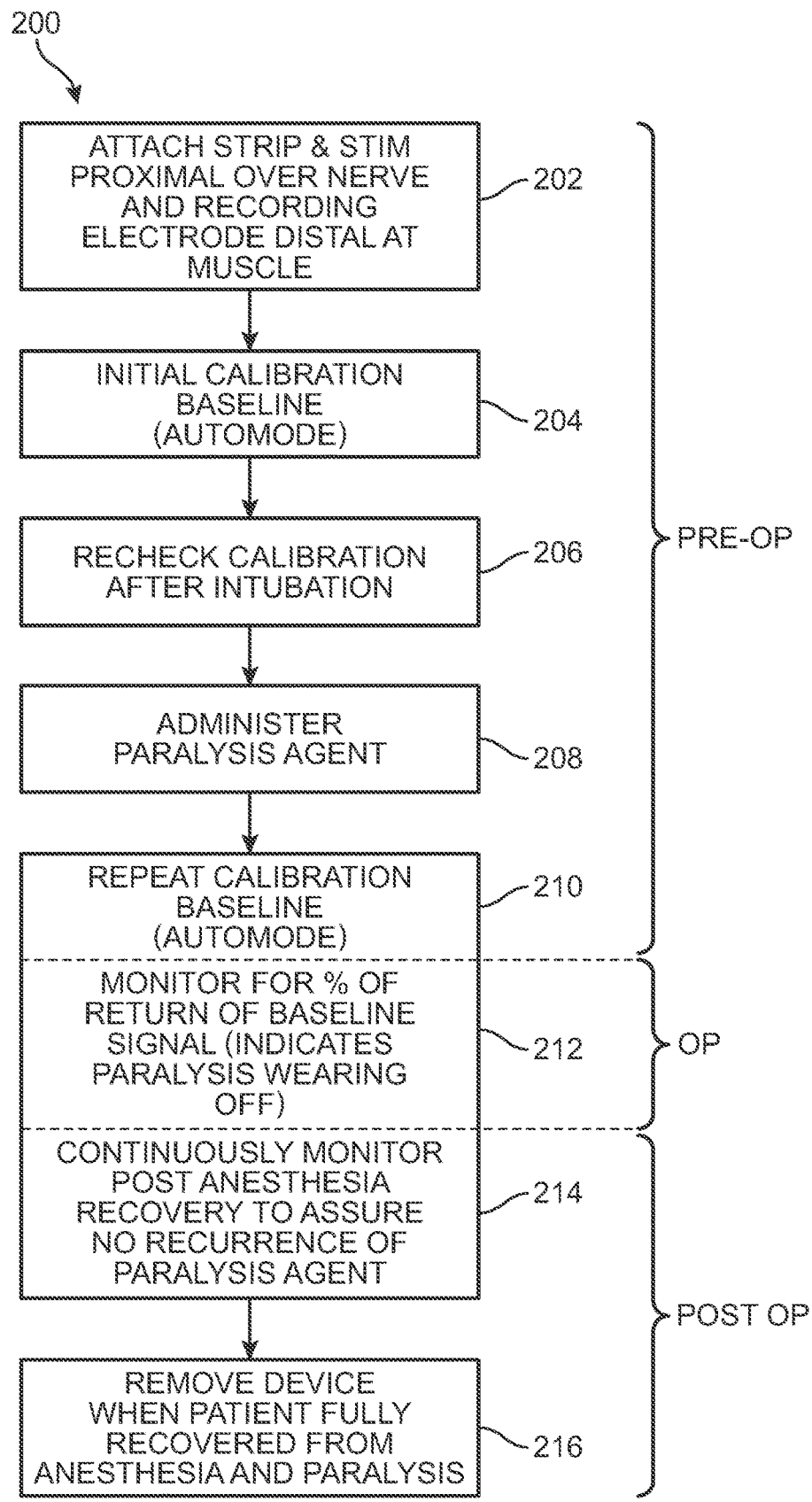
FIG. 2 is flow chart illustrating an exemplary overall method of operation of the exemplary paralysis monitoring systems of FIG. 1.
Figure 3:
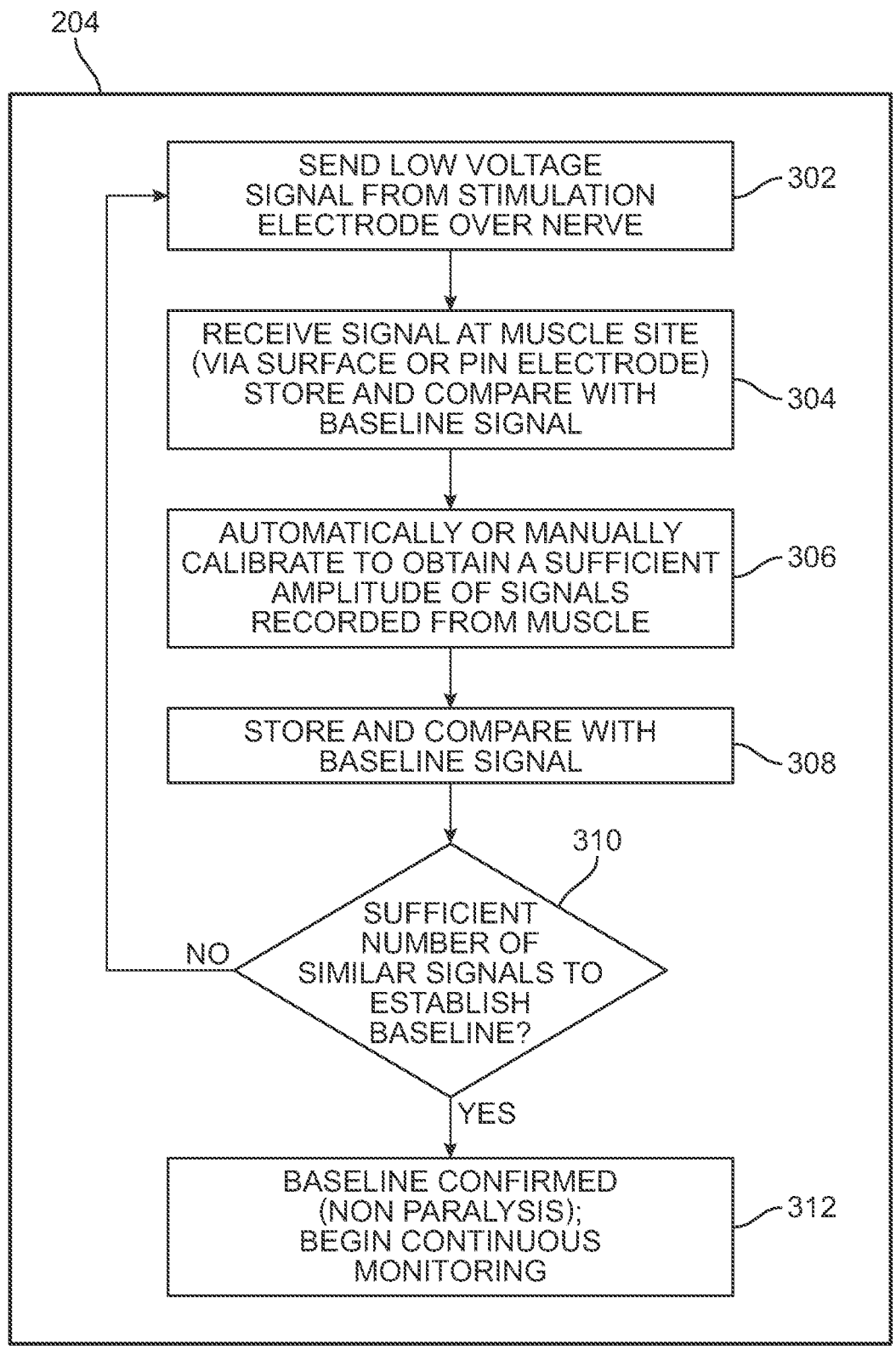
FIG. 3 is a flow chart illustrating in more detail the initialization and preparation for continuous monitoring step of the method of operation of the paralysis monitoring system shown in FIG. 2.
Figure 4:
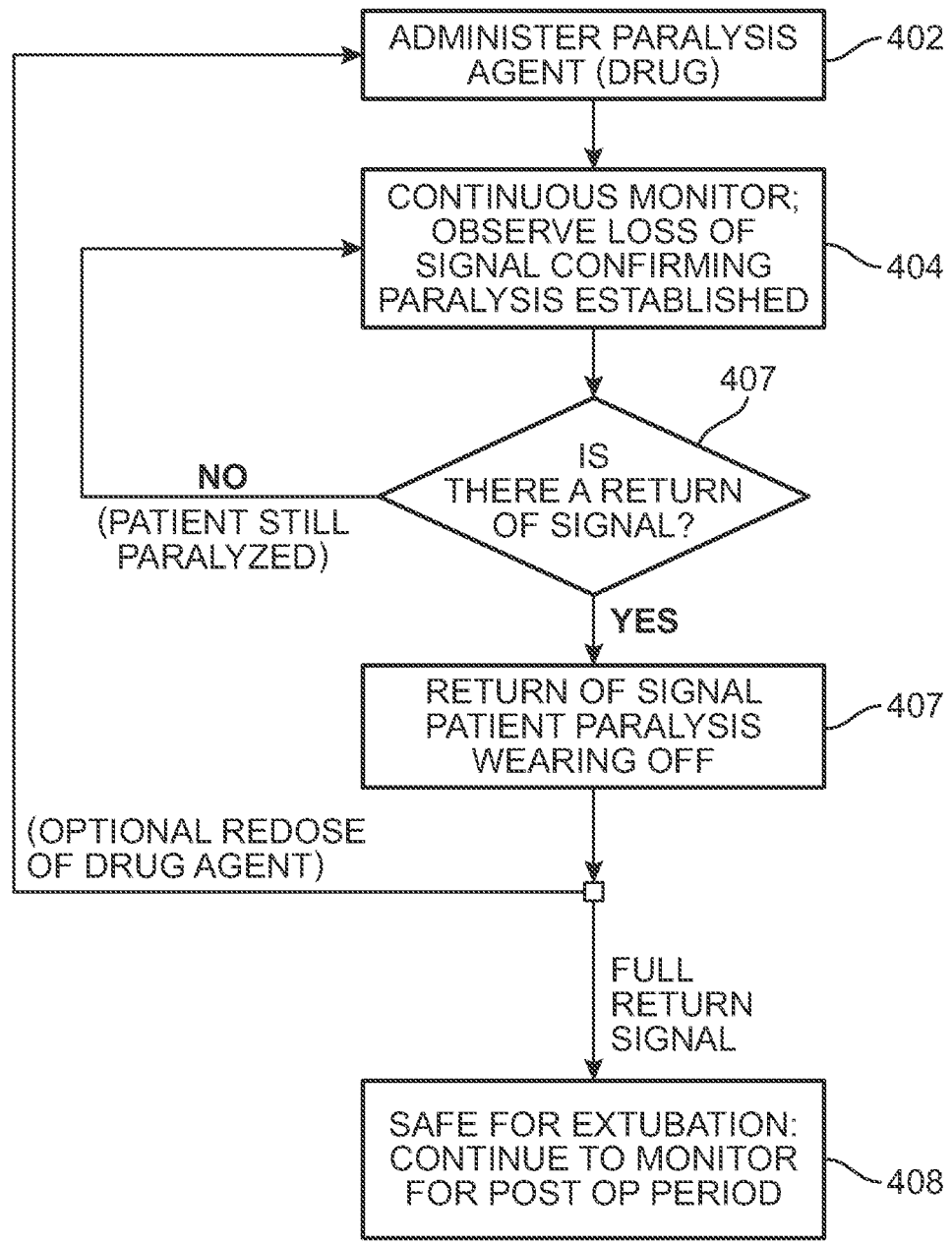
FIG. 4 is a flow chart illustrating in more detail the steps of continuously monitoring the onset of paralysis, paralysis after onset and recovery steps of the method of operation of the paralysis monitoring system shown in FIG. 2.

In order to better understand the disclosed embodiments, the process through which monitoring system 100 is operated and utilized is generally represented in the flow diagrams of FIGS. 2-4. FIG. 2 represents an overview of an embodiment of a method of using the paralysis monitoring system during the pre-operation, operation, and post-operation stages. Referring to FIG. 2, a first step 202 may involve attaching paralysis monitoring system to the patient. In other words, the stimulation device and the recording device can be positioned directly on or into the skin of the patient. This can include placement of a strip that is attached to both the stimulation probe and the recording electrode. In some embodiments, the stimulation probe is positioned proximally to the nerve that is being stimulated, and the recording electrode is positioned distally at the muscle. Depending on the procedure, the appropriate anatomy or position of the monitoring device can vary, though typically placement would be over the ulnar nerve in the forearm or over the tibial nerve in the leg and alternatively as well could be used on the facial nerve. Those are the three most accessible access points. But is contemplated that any other place where a major nerve could be stimulated and a response obtained would be a possibility from median to femoral to sciatic to almost any nerve. In some embodiments, there may be a prior, concurrent, or later step of inducing anesthesia or a type of sedation in the patient.

A second step 204 can comprise establishing an initial calibration baseline. Further detail regarding second step 204 will be described in conjunction with the description of FIG. 3 below.

The initialization of the monitoring system can also occur during this step, as well as general preparation for continuous monitoring. A third step 206 comprises rechecking the calibration baseline if the patient is intubated. In a fourth step 208, a paralytic agent is administered to the patient. In a fifth step 210, the paralysis monitoring system continuously monitors the patient's muscle responses to determine the onset of paralysis following the administration of a paralysis agent. Thus, after the system determines there is sufficient paralysis to begin the operation or surgical procedure, the system can be configured to continuously monitor the paralysis of the patient during the surgical procedure. In some embodiments, the stimulation device repeatedly provides stimulations to the patient at the pre-programmed low intensity on an automated cycling schedule. In other embodiments, the schedule could be run at different frequencies. For example, in one embodiment the stimulation device can run between every 1-3 seconds up to every 1-4 minutes, providing feedback and a continuous monitoring of the patient on a display screen.

Typically, upon administration of a paralysis agent, the spike discharge signal (produced by electrical stimulation of the target nerve(s) and being recorded by the monitoring system) will diminish and can be entirely lost. In one embodiment, such a signal loss corresponds to a confirmation that paralysis of the patient has occurred. In other words, as neuromuscular receptors and junctions become blocked, when the nerve is stimulated, the patient's muscle response decreases or is lost. While the paralytic agent is in the patient's system, the stimulus shocks do not produce a response in the muscle. Throughout the procedure, intermittent stimulus shocks may be administered, providing for an ongoing, continuous monitoring of the patient.

As the administered paralysis agent(s) wears off, a percentage return of the response signal will occur. Thus, a response to the single pulse stimuli begins to return, indicating that the functional phase of the paralytic agent is progressively declining. In a sixth step 212, the paralysis monitoring system continuously monitors the recovery of the patient and the return of muscle responses as shown by spike discharges. In some embodiments, the percentage return that is associated with the recovery of the patient's muscle activity can be approximately 50%. In other embodiments, the range may be between 20% and 80%. Thus, the stimulus device continues to administer intermittent single shock pulses to the patient, and the recording device continuously records the electrical activity of the muscles throughout the operation, and after the operation. The system can be configured to automatically transmit pulses to the patient and notify a user if there is any return of the response signal. In an optional seventh step 214, the system can continuously monitor the patient in the post-anesthesia stage, ensuring that there is no recurrence of paralysis or a reactivation of the effects of the paralytic agent.

As a patient begins to regain the ability to move (as the paralysis reverses), there is an increasing graded percentage of return of the signal being measured by the monitoring system. Over time, the recorded responses to the stimulation impulses increase in intensity, until eventually returning to the baseline level, providing verification that paralysis has fully worn off. After this occurs, the paralysis monitoring system can be removed from the patient, as represented in an eighth step 216. Furthermore, it should be understood that after the procedure (i.e., during the post-operation stage) the paralysis monitoring device can continue to stimulate nerve (s) in a patient and record any corresponding muscle activity.

Thus, the monitoring system can be used to ensure the patient maintains a certain paralysis level as needed by a surgeon to complete the procedure and can also be used to ascertain the amount of paralysis residual at the end of the procedure. Thus, the monitoring system can help determine whether there has been full metabolism of the paralytic agent and whether the patient is safe to extubate.

In some embodiments, the monitoring system can be left in position with an alarm in the postoperative recovery room, providing continuous monitoring of the patient's paralysis. For example, if a reversal agent is used and re-paralysis occurs, an alarm can be triggered if there is a loss of the signal or partial loss of the signal, indicating that the paralysis is returning inadvertently.

As noted above, in some embodiments, the post-operative process can be similar to the operation of the system during the procedure or operation. For example, once a patient has entered the post-operative stage, the paralysis monitoring system may remain attached or connected to the patient. The system may continue to transmit low voltage electrical impulses to the patient as well as continuously monitor the muscle activity of the patient. Often a patient remains in partial paralysis following the completion of the procedure. As noted above, in some embodiments, the monitoring system may also be utilized as a postoperative paralysis monitoring system. In the cases in which the patient has awakened from anesthesia yet remains paralyzed, the monitoring system may continue to show profound paralysis while other signs of waking up would be registered, such as increased heart rate, increased blood pressure, and/or some jerky or twitching motions. Thus, the monitoring system can indicate that the patient is awakening but is too paralyzed to move functionally. In one embodiment, the paralysis monitoring system can be configured with an alarm or other type of alert that the spike discharge recordings have begun to indicate a return of response signals or muscle activity, or an alarm that alerts the healthcare professional that the patient has begun to awaken yet remains in paralysis.

The monitoring system can be utilized regardless of whether a reversal agent is used.

A reversal agent or drug is typically a competitive antagonist that competes for a binding site. Thus, reversal agents are generally administered to block a paralyzing drug molecule from attaching to a cell surface where it was exerting its effect. The reversal agents can act to speed the muscle recovery process, but there are significant side effects associated with the use of reversal agents, and reversal agents may not be reliable, and are certainly not as reliable as the passage of time in decreasing the effects of paralytic agents. As noted above, there are many risks associated with the patient's recovery from anesthesia and paralysis, and a system that can continuously monitor the return of muscle activity during recovery can help prevent unnecessary trauma to a patient.

FIG. 3 illustrates in more detail the exemplary initialization and preparation for continuous monitoring step 204. In FIG. 3, in order to initialize and begin continuous monitoring of a patient, a low voltage signal may be transmitted from the stimulation device or electrode to the nerve in a first step 302. The low voltage signal can cause a change in muscle activity in the patient, which is received as an electrical signal by the recording device in a second step 304. In some embodiments, this can involve the monitoring system being turned on with a standard series of single impulses, and baseline stimulation responses being recorded, as shown in a third step 306. Thus, in some embodiments, the monitoring system applies an intermittent pulse that is repeated periodically, e.g., every several seconds or other time period. The monitoring system measures and records the response to the single pulse stimulation to determine the effect of the paralytic agent.

The baseline stimulation runs can be automated or manually operated in different embodiments. For example, an automated mode could transmit stimulations through an incremental pre-programmed 'auto-cycle' of voltage levels (for example, from 0.1 my to 2.0 my, etc.). In one embodiment, the cycle would increase the intensity of stimulation until the system registered a predetermined response at the muscular interface that indicated a good connection of the device for that given patient and system placement.

The continuously recorded spike discharge activity can be stored and compared with previously recorded spike discharge activity in a fourth step 308. In a fifth step 310, the paralysis monitoring system evaluates whether there have been a sufficient number of similar recorded signals to establish a baseline recording for that patient. If the answer is yes, the baseline is established in a sixth step 312. If there are not yet a sufficient number of signals recorded by the system, the system will repeat the application of low voltage signals to record evoked muscle responses until a baseline recording can be established.

In different embodiments, during a baseline recording, a direct spike focus is obtained that corresponds to a baseline mode as well as a direct up and direct down impulse that is the result of the direct shock stimulus (provided by the stimulation device). The millivolt stimulus (e.g., in the range 0.5-1.5 millivolts, or up to as high as 3 to 4 millivolts, in some cases) is administered to the patient and the monitoring system analyzes the readings until a spike of certain height over background noise that it is repeatable and obtainable is recorded. In some embodiments, the spike discharge is at least 200% above the background noise level spike. In one embodiment, the spike discharge is at least 500% above the background noise level spike, such that the baseline spike discharge is easily obtainable. In different embodiments, the baseline recording allows the monitoring system to account for patient variables, such as skin temperature, skin depth, the fatty content of skin, and/or the relative distances the stimulation probe and recording probe are located from the nerve, and other such variables. Thus, slight differences in electrodes, individual characteristics such as subcutaneous fat, skin thickness, or oil and/or hair on the skin surface, and other factors that vary the levels of electrode impedance can significantly modify the values of the electrical discharge. By appropriate selection of spike discharge levels over noise, the monitoring system automatically accounts for these type of variables.

In some embodiments, baseline recordings could also be used to filter out fasciculations, which are brief, spontaneous contractions that can affect muscle fibers, often causing a flicker of movement under the skin. In one embodiment, such background noise could be filtered out with a timing mechanism that would time the stimulation pulse to the signal and filter out background noise fasciculations. Thus, a baseline recording by the monitoring system provides an indication of the of the individual's muscle activity that can be used to calibrate the signal. In other words, the baseline recording can serve as a basis of comparison for subsequent data collection. Because these types of factors can also affect the amount of current that is required to provide accurate stimulation, the baseline recording offers an advantageous reference point throughout the monitoring process.

Further detail regarding exemplary third step 210 through fifth step 210 is provided in the flow diagram of FIG. 4. Referring to FIG. 4, following administration of a paralysis agent in a first step 402, it becomes of paramount importance to ascertain whether the patient has become paralyzed. As noted above, the paralysis monitoring system can intermittently send a low voltage signal to the patient's nerves, and the recording device receives and records any spike discharge signal in order to monitor the condition of the patient. Thus, the system can continuously monitor the patient to verify a loss of signal and confirm that paralysis has been established in a second step 404.

The received response signal (RS) may be compared to the baseline spike discharge recording using conventional circuitry such as comparators, memories and the like. If the received signal is less than the baseline spike discharge recording by a specified amount or delta, the system determines that the patient has been successfully paralyzed, and the surgical procedure may begin. If the difference between the received signal and the baseline spike discharge recording is insufficient, the system continues to monitor the muscle activity. In a third step 406, the system determines whether a signal is returning. If there is no signal, the system continues to monitor the patient and verify that paralysis is established. If a signal returns, indicating the paralysis is wearing off as in step 407, the system can continue to monitor the patient until the paralysis has been fully reversed and the condition of the patient is deemed safe for extubation, as shown in a fourth step 408. In some embodiments, monitoring can continue during the post-operative period as well. However, in other embodiments, the patient may instead be optionally re-dosed to return the patient to a state of paralysis.

If additional paralysis agent is administered, it should be understood that there would be a repeat loss of the signal when the patient becomes fully re-paralyzed. However, in many cases, total paralysis may not be required by the procedure. In some instances, for example, a healthcare professional may determine that an 80% reduction in the signal intensity or height of the spike discharge is sufficient. In other words, the percentage reduction need not be 100% in order for a patient to be deemed clinically paralyzed and able to continue the surgical therapy. As the additional paralytic agent wears off entirely, there is a return of the signal to complete baseline, indicating a 100% functional return to the preoperative level, assuming no other changes have occurred in the patient which might affect the response signals. For example, if the patient is very cold there can be effects upon the ability to stimulate the nerve.

Thus, during post-surgery recording, the spike discharges would be displayed as 100% of the baseline recording level, corresponding to the condition in which the patient is awake and able to move normally. If the patient is still weak but able to move somewhat, it is anticipated that the spike discharge will be a percentage of normal (for example, between 40% to 80% of the baseline recording level). However, the additional or repeat dosing step depicted in FIG. 4 should be understood to be optional, and continuous monitoring can occur without any additional paralytic agent.

Figure 5:
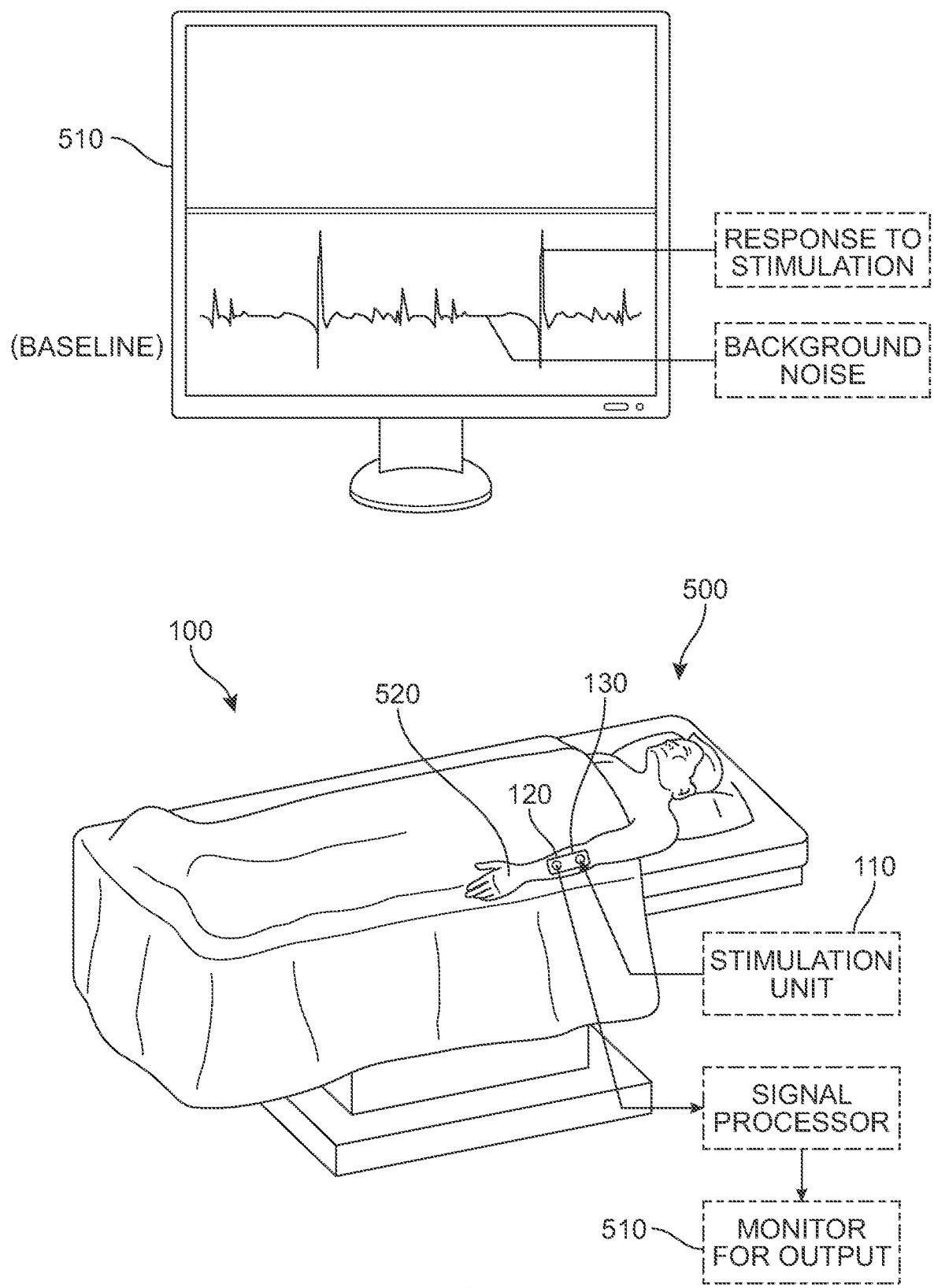
FIG. 5 illustrates an exemplary spike discharge recording according the principles of the invention prior to administration of a paralysis agent.

In order to provide greater clarity, FIGS. 5-8 illustrate embodiments of the paralysis monitoring system during a typical procedure with exemplary spike discharge readings. As shown in FIG. 5, the monitoring system 100 has been placed on or attached to a patient 500. In this example, monitoring system 100 has been positioned along an arm 520 of patient 500. Stimulation electrode device 110 and recording device 120 are arranged along strip 130 and are disposed on a nerve such as the ulnar nerve in the forearm. However, in other embodiments, monitoring system 100 can be disposed along any other portion of a patient's anatomy that enable access to stimulate and response from a major nerve including median to femoral to sciatic to almost any nerve. Furthermore, it can be seen that monitoring system components (such as stimulation electrode device 110 and/or recording device 120) can be connected to a signal processor, which can also be connected to a monitor or display 510.

Figure 6:
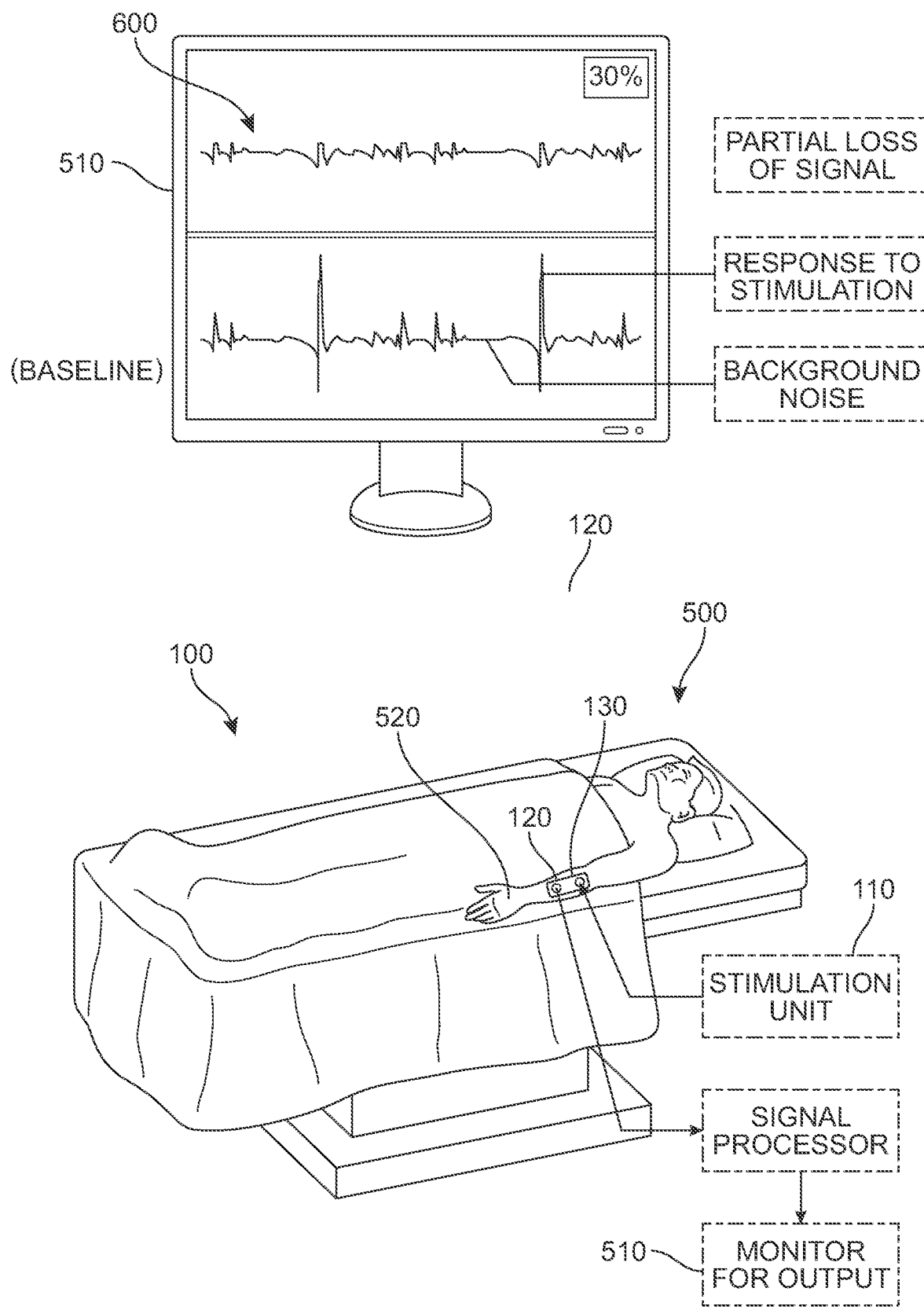
FIG. 6 illustrates an exemplary spike discharge recording following the administration of a paralysis agent.

As monitoring system 100 is activated, a baseline recording of the muscle responses of patient 500 is taken, as described earlier with respect to FIG. 4. In FIG. 5 it can be seen that a display 510 includes only the patient's baseline signal (which was established and recorded earlier). After a paralysis agent is administered, the spike discharge recording changes, as shown in the example of FIG. 6, where a paralysis spike discharge recording 600 on display 510 illustrates how the signal is effectively 'lost' as muscle responses become minimal as paralysis sets in. The approximate signal loss relative to the baseline signal is displayed as a percentage, such as 30% shown in FIG. 6, although in other embodiments, different graphical icons or images can be presented, such as a pie chart or other visual indicators. The amount of signal loss can vary throughout the procedure.

Figure 7:
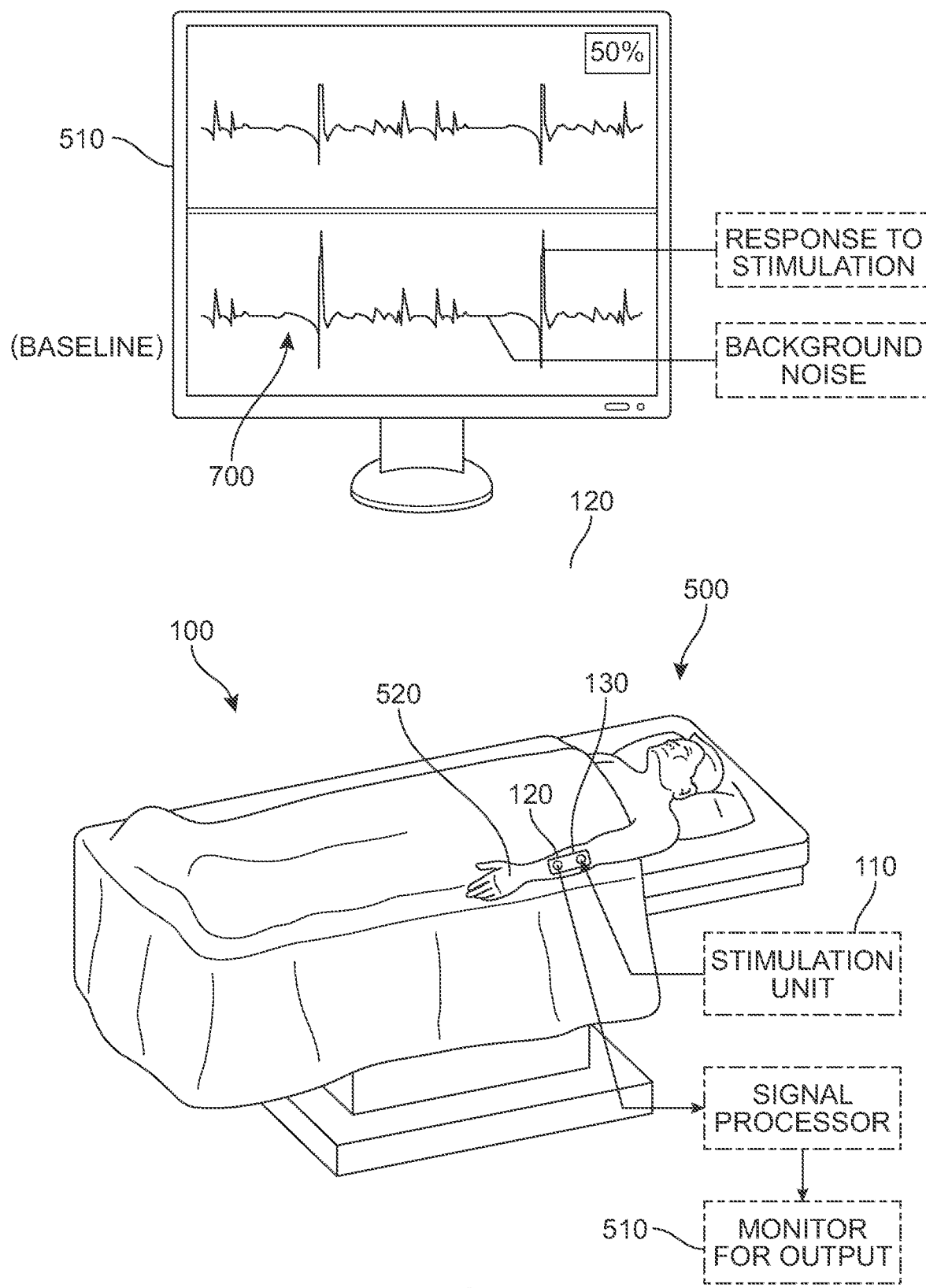
FIG. 7 illustrates an exemplary spike discharge recording as the paralysis agent wears off.

Over time, the paralysis agent can wear off, and there is a progressive return of muscle activity, represented in the embodiment of FIG. 7 as a recovering spike discharge recording 700. FIG. 7 shows that the loss of signal is increased from 30% in FIG. 6 to 50%. Eventually the spike discharge signal grows in strength until the muscle activity returns to levels associated with the baseline spike discharge recording. In some cases, as noted above, muscle activity can begin to return during a procedure. When a paralytic agent wears off during surgery, the monitoring system is able to determine the level of reversibility in the patient.

Referring to FIG. 7, patient 500 is shown as a progressive return of motor activity is occurring. Monitoring system 100 can assess and evaluate the return of motor activity by the increasing percentage of spike foci, to help determine whether additional micro-doses of paralytic agent are needed. In some embodiments, this determination can be based in part on factors inputted by a user into the system such as the length of the case and/or the patient's sensitivities or metabolism.

In different embodiments, the monitoring system can comprise commercially available components that are used routinely in neurostimulation and/or EMG recording. In addition, as noted above, the monitoring system can include a computer or other processing unit that can be configured to process the signal, to run the autocalibration cycle, and/or to print out or display the percentage of baseline activity available and send that information to the anesthesia machine.

FIG. 8 shows examples of a surface electrode for stimulation of a nerve. An example of a commercially available stimulus generator 802 that may be used in embodiments is the Stimuplex HNS-12 model made by B. Braun shown in FIG. 9, which may be operated to stimulate nerves between 0.1 to 4 mV in accordance with the principles of the invention. The surface and recording electrodes may be commercially available electrodes, such those packaged with Stimuplex HNS-12 stimulus generator. Furthermore, in some embodiments, a commercially available monopolar point impulse generator 804, such as the Direct Nerve Stimulator Probe available from Friendship Medical Electronics shown in FIG. 10, can be utilized to stimulate the nerve. In other embodiments, a bipolar stimulating probe may be used, such as the Bipolar Nerve Stimulator Probe, Friendship Medical Electronics. The monitoring system can also include a computer processor and recording monitor unit (such as the commercially available Nicolet Viking Viasas recorder monitor), which can be used to record, print and analyze EMG waveforms. In some embodiments, an additional surface electrode could be applied in FIG. 8 for EMG recording.

In different embodiments, the stimulus device could provide either a standard input or a variable self-calibrating device. In addition, in some embodiments, the monitoring system could include stimulus probes placed in different locations. Furthermore, the disclosed embodiments could include magnetic stimulation to the brain or more proximal nerves, could involve alternative recording techniques for EMG through the skin with the standard pin recordings, and/or could involve so different analysis endpoints in the processing to state the percentage of paralysis that are present.

Some of the concepts described herein have been tested by the inventor. The test involved the use of standard, commercially available equipment for nerve stimulation. During testing, stimulus probes were placed on the skin of the inventor using the Stimuplex HNS-12 model generator shown in FIG. 9 and a nerve in the arm was stimulated between 0.1 mV to 0.2 mV. A strong response in the muscle interface was produced and recorded. During the testing, there was no sensation from the stimulus probe voltage. The stimulus voltage was increased progressively to the level typically used in the conventional train-of-four technique, which caused a physical twitch in the arm, whereby the stimulus became painful and left a persisting tingling feeling in the arm ranging from a few minutes to half an hour or more. In addition, during this initial testing, the monitoring system prototype was also tested for instance recording as well as the surrounding muscles both proximal and lateral to the plane of intervention to make sure there was no noise or a spread in the impulse, to ensure that the recording accurately represented neural-to-motor interface of the particular nerve and also to look at ranges and repeatability.

Systems constructed according to the inventive principles discussed herein provide a considerable improvement over conventional techniques by allowing a continuous monitoring including providing a printout to the anesthesiologist. The monitoring system of the invention determines (a) the depth of paralysis present, (b) the level of reversibility of the patient, and/or (c) a safety margin for extubation. Furthermore, the monitoring system provides for continuous monitoring in the postoperative period, which helps prevent postoperative re-paralysis and/or death from respiratory arrest. Thus, monitoring systems constructed according to the principles of the invention provide a dramatic decrease in the risks associated with paralysis during procedures requiring anesthesia and/or simplify the process of paralysis monitoring in a standardizable fashion. In addition, monitoring systems of the invention overcome disadvantages of conventional paralysis monitoring techniques, which rely upon crude visual observation of muscle responses, and do not account for the variability of patient physical characteristics such as skin thickness, temperature of the patient's extremities, etc., with a reliable neuromuscular recording possible with the inventive concepts. As noted earlier, it is also essential to ascertain that the effects of neuromuscular blocking drugs have worn off or are reversed before the patient regains consciousness. For example, even after paralytic agents wear off, residual paralysis remains an issue, in spite of the availability of shorter-acting neuromuscular blocking drugs. Thus, monitoring system embodiments of the invention dramatically increase the safety of the patient and help prevent historically multiple postoperative deaths that are recorded per year, as well as postoperative respiratory arrests.

Furthermore, it should be understood that in some embodiments the auto calibration system as disclosed herein obtains a baseline stimulus that takes into account (a) the temperature of the skin; (b) the distance the probe may be from the nerve; and (c) the contact of the recording electrode (i.e., whether surface or pin will determine adequacy of the recorded stimulus). In an exemplary embodiment, the baseline recording would be at least ten times the background noise. Furthermore, the baseline calibration would confirm the proper placement of the electrode patch, ensuring that the electrode will generate a stimulus/response in an acceptable range of stimulation. If an adequate response is not obtained the patch would need to be repositioned or the contacts checked. However, in other embodiments, the range can vary. Once the baseline is established and the electrode placement is correct, that signal would become the baseline signal to which continuous monitoring signal would be compared. In other words, the loss of that baseline indicates a paralyzed state. As a patient begins to recover, the paralysis wears off in a graded or a percentage fashion. Once baseline is reestablished, the patient can be safely extubated. Thus, the end of anesthesia would be pending a complete return of the signal to baseline. In addition, postoperative monitoring is important because often a reversal agent is used which is known to work for a short duration, but there may be residual paralytic agent that outlasted the procedure, and the patient may slip back into a partial paralyzed state.

In some embodiments, the use of the monitoring system comprises a sequence of steps. A first step comprises obtaining a baseline after sedation, prior to the administration of any paralytic agents. A second step comprises switching on continuous monitoring after the auto calibration is complete. A third step involves a continuous monitor and observation of the loss of signal during onset of a paralytic agent. A fourth step occurs when the continuous monitor records the beginning of a percentage of return of the spike discharge, indicating the paralysis agent is wearing off. In a fifth step, an anesthesiologist can determine whether to administer more agent, for example, in the case where the surgeon requires additional time to complete the procedure. A sixth step involves confirmation of a return of the full baseline signal prior to ending in a static procedure, and the extubation of the patient. The seventh step comprises continuous monitoring in the recovery room until the patient is fully awake, in order to avoid a relapse to paralysis.

In the presence of a neuromuscular blockade an operator of a paralysis monitoring system would not expect to see a strong response to a stimulating voltage. Therefore, to ensure the monitoring system is operating properly, some embodiments may include provisions for taking an independent measurement or reading of electrical signals from a location away from a target muscle group. For example, measuring electrical signals from nearby soft tissue (e.g., nearby to, but not on, the target muscle group) can provide an independent reading from the recording electrodes located over the target muscle group. The independent measurement may record an electric signal that is distinct from the signal detected at the muscles during stimulation. The presence of an electrical signal that appears to correspond with the timing (or other characteristic features) of any electrical signals generated at a stimulating device may help confirm that the stimulating device is not malfunctioning even when a low response is seen at the muscle group (because of a neuromuscular blockade).

Figure 11:
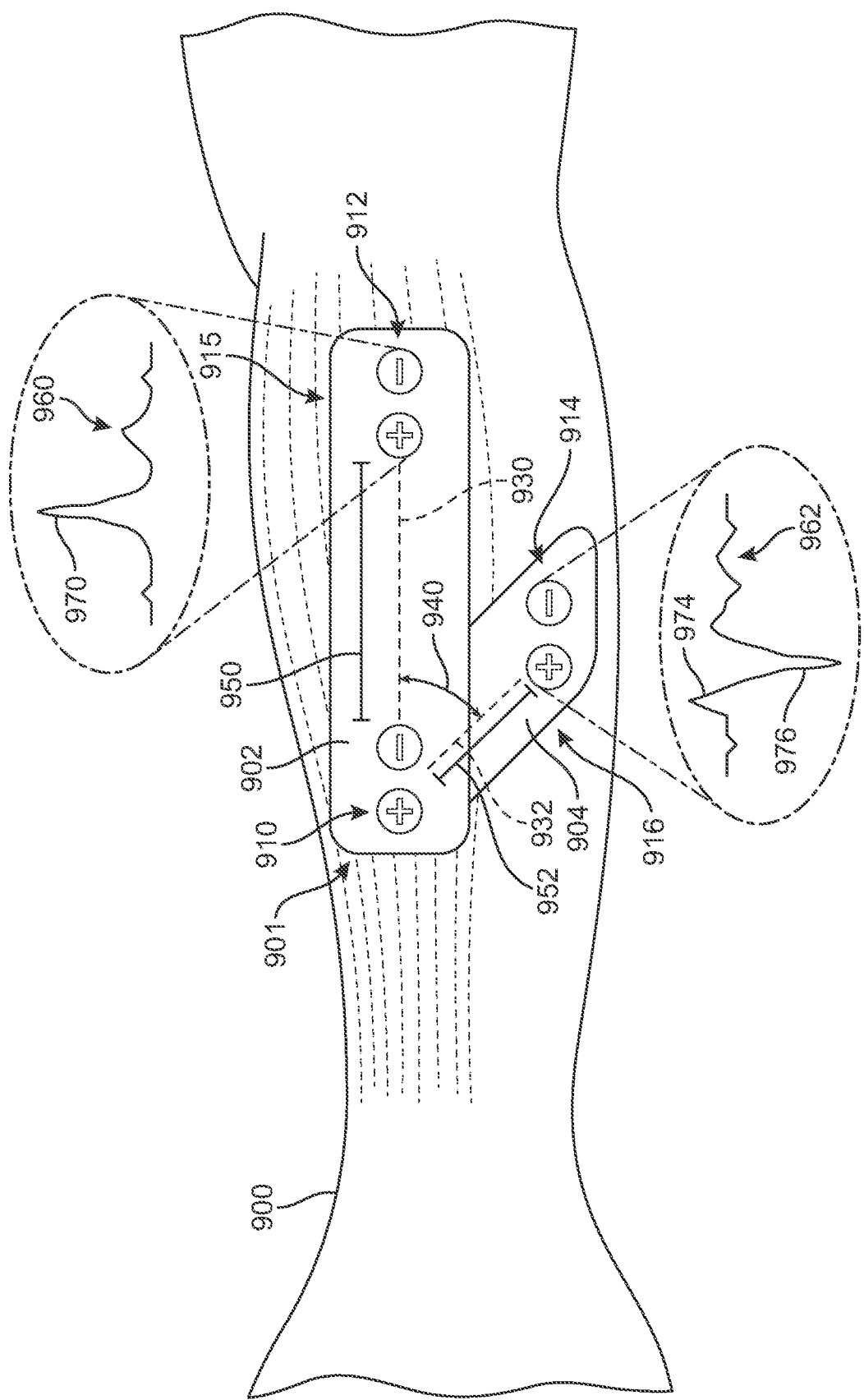
FIG. 11 is a schematic view of another embodiment of a paralysis monitoring system applied over a limb.

FIG. 11 is a schematic view of an embodiment of a patient's arm 900. A monitoring system 901 includes a stimulation electrode device 910 (or simply "stimulation device") and primary recording device 912. Stimulation device 910 and primary recording device 912 are arranged along a first strip 902 and are disposed on a nerve such as the ulnar nerve in the forearm. Primary recording device 912 may be disposed over a target muscle region 915, which corresponds to the muscles that may be directly affected by the stimulation of the nerve targeted by stimulation device 910.

Monitoring system 901 includes a secondary recording device 914. In some embodiments, secondary recording device 914 is disposed on a second strip 904 that may be attached to first strip 902. Secondary recording device 914 may be disposed over a soft tissue region 916 that is displaced from target muscle region 915.

Although each of stimulation device 910, primary recording device 912 and secondary recording device 914 are shown schematically as electrode devices, the exemplary embodiment could utilize any kind of stimulation device and/or recording device. In some cases, needles or other subcutaneous probes could be used. Moreover, any kind of stimulation and/or recording device disclosed previously with respect to the embodiment of FIGS. 1-10 could also be used.

In different embodiments, the locations of each recording device relative to a stimulation device could vary. In some embodiments, each recording device could be disposed on a common axis with a stimulation device. In other embodiments, each recording device may be located on a different axis with respect to a stimulation device. In the embodiment shown in FIG. 11, first strip 902 may be characterized by a lengthwise axis 930 that runs approximately parallel with the length of arm 900. In contrast, second strip 904 may have a second lengthwise axis 932 that is oriented at an angle to lengthwise axis 930. In some cases, axis 930 and axis 932 may be disposed at an angle 940 with respect to one another. In some cases, angle 940 could range between approximately 0 and 90 degrees. In some embodiments, angle 940 may range between approximately 30 and 60 degrees. In one embodiment angle 940 have a value of approximately 45 degrees.

Each recording device can also be located a different overall distance from a stimulation device. In some embodiments, a primary recording device (i.e., a device disposed over a target muscle region) may be disposed closer than a secondary recording device (i.e., a device disposed over another soft tissue region that is different from the target muscle region) to a stimulation device. In other embodiments, a primary recording device could be disposed further from a stimulation device than a secondary recording device. In still other embodiments, a primary recording device and a secondary recording device could be approximately equidistant from a stimulation device. In the exemplary embodiment shown in FIG. 11, primary recording device 912 is disposed further from stimulation device 910 than secondary recording device 914. Specifically, primary recording device 912 may be disposed a first recording distance 950 from stimulation device 910 and secondary recording device 914 may be disposed a second recording distance 952 from stimulation device 910. In some embodiments, second recording distance 952 may be approximately in a range between 30% and 70% of first recording distance 950.

In some cases, the exact location (and relative distance to a stimulation device) of each recording device can be selected according to factors including stimulation voltage levels (and/or currents), patient characteristics (such as body fat, size of target muscle group, etc.), sensitivity of the recording devices as well as possibly other parameters. It may be appreciated that locating a secondary recording device away from the target muscle group may allow for recording of electrical signals that may be independent of the muscle response (which may be affected by neuromuscular blockades). Such independently recorded signals can be used to determine that a monitoring system is operating properly (e.g., that a stimulating device is functioning correctly and sending out electrical pulses of desired voltages and intervals).

FIG. 11 includes two schematic views of signals that have been independently recorded by primary recording device 912 and secondary recording device 914. These include a first electrical signal 960 detected at primary recording device 912 and a second electrical signal 962 detected at secondary recording device 914. It may be appreciated that the exemplary signals are shown for schematic purposes and they may or may not be visible on a monitoring screen during a procedure in some embodiments. As in the embodiments described above and shown in FIG. 5, the components of monitoring system 901 (such as stimulation device 910, primary recording device 912 and secondary recording device 914 may connected to a signal processor (not shown in FIG. 11), which can also be connected to a monitor or display.

As seen in FIG. 11, first electrical signal 960 and second electrical signal 962 may have different waveforms or waveform characteristics. For example, first electrical signal 960 includes regions of baseline noise with a large peak 970 corresponding to a muscle response. Second electrical signal 962 includes a moderately sized peak 974 followed immediately by a large dip 976. It may be appreciated that first electrical signal 960 and second electrical signal 962 have distinct waveforms that may not only be distinguished by quantitative analysis but may also be qualitatively distinct.

It may be appreciated that in some cases, electrical signals detected at secondary recording device 914 (e.g., second electrical signal 962) may be associated with electrical signals generated by stimulation device 910 (i.e., low voltage electrical impulses) that have spread to surrounding tissue but have not evoked a muscle response. That is, as low voltage impulses are generated at stimulation device 910, some of the electrical energy that is generated may stimulate the underlying nerve (and thus evoke a muscle response via the nerve), and some of the electrical energy may be dissipated into surrounding tissue without stimulating the nerve. It is this latter part of the electrical signal that may, in some cases, be detected by second recording device 914. Alternatively, in some cases second recording device 914 may detect electrical energy that has been generated at a nerve and/or at a muscle. It should be understood that while the underlying source (or sources) of the electrical signal(s) measured at the second recording device 914 could vary in different situations, the monitoring system may be useful whenever the signals detected at second recording device 914 are substantially different from the signals detected at first recording device 912 (in a quantitative and/or qualitative sense).

Moreover, it may be appreciated that the features (e.g., peak 974 and dip 976) recorded by secondary recording device 914 are sufficiently distinct from any background or baseline noise so as to be immediately identifiable as a response to a pulse from stimulation device 910. In trial uses of the exemplary device such waveforms have been observed to have a distinct characteristic from muscle response waveforms. It may be inferred therefore that these signals are an artifact of the system that is distinct from the electrical signals generated at the muscle during contraction. For reference, these distinctive waveforms measured at location away from a target muscle group may be referred to as "stimulation artifacts" as they allow a doctor or technician to infer the presence of a stimulating signal but are unrelated, or indirectly related, to direct muscle response signals.

Using the above embodiment of a monitoring system, it is possible for a doctor or technician to confirm that a monitoring system is operating as expected. Specifically, a doctor or technician may observe a response signal near the stimulation source even when a neuromuscular blockade prevents a primary recording device from detecting evidence of electrical signals above the baseline signal.

Figure 12:
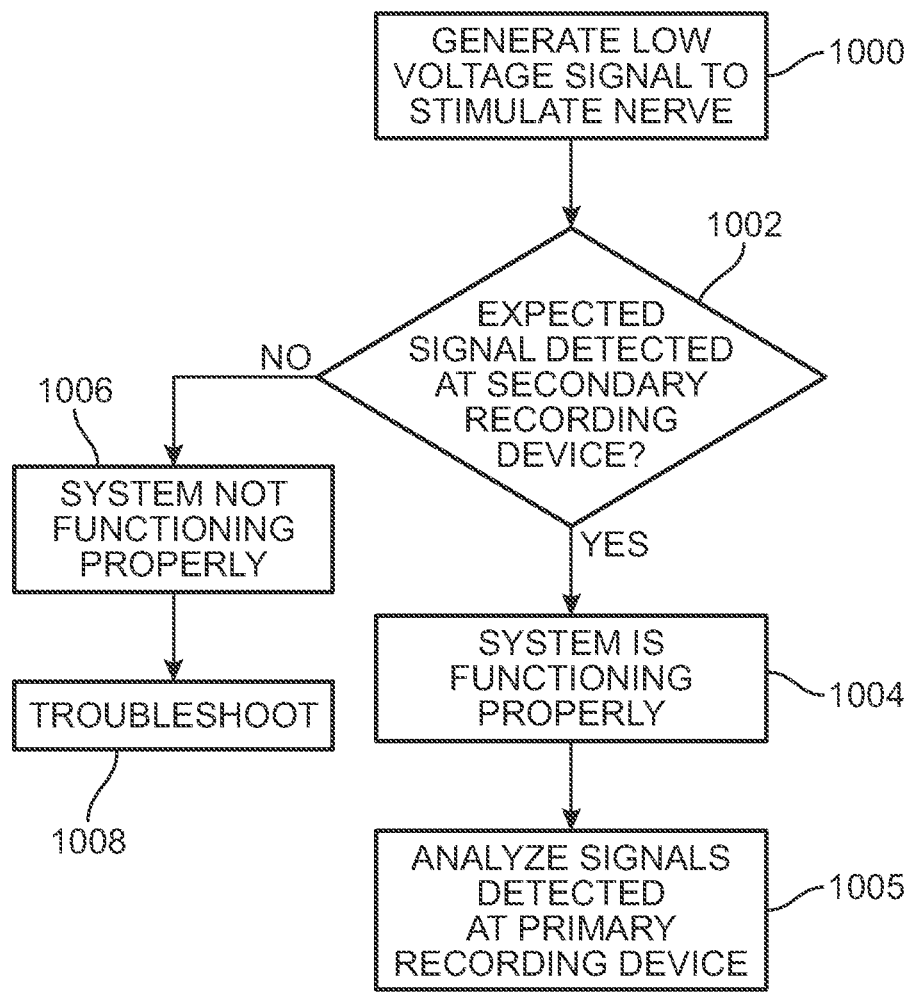
FIG. 12 is a schematic view of a process for checking the functionality of a paralysis monitoring system, according to an embodiment.

FIG. 12 is a schematic view of a process of using a secondary recording device to confirm that a monitoring system is operating properly. It may be appreciated that some or all of the following steps could be combined with any of the processes described above and shown, for example, in FIGS. 2-4. In some embodiments, the following steps for checking that a monitoring system is functioning properly could be done towards the beginning of an overall paralysis monitoring process. In other embodiments, the following steps could be done throughout a monitoring process either at regular intervals or continuously. Moreover, it may be understood that the following process could be performed manually by a doctor or technician (i.e., by pushing buttons and visibly monitoring responses), automatically by a machine, and/or some combination of manual and automated steps.

In a first step 1000, a stimulation device (e.g., stimulation device 910) may be instructed to generate one or more low voltage impulses to stimulate an underlying nerve. As described above, the low voltage impulse may be at a level that is insufficient to cause visible muscle twitch or contraction. Next, in a step 1002, the operating condition of the system may be checked by confirming that a signal has been received at a secondary recording device (e.g., recording device 914) that is located away from the target muscle region. Moreover, during this step, the signal may be analyzed to determine if the signal is consistent with a low voltage impulse being generated by the stimulation device. As previously discussed, in some cases this can be done manually by visually inspecting that the second recording device is measuring signals with qualitatively distinct waveforms known to be associated with stimulation impulses.

If, during step 1002, the expected signal is detected at the second recording device, it may be determined that the system is functioning properly in step 1004. At this point the process may proceed to analyzing the signals detected at the primary recording device to determine a paralysis level during step 1005. This step may include any of the processes described above and shown in FIGS. 2-4 for paralysis monitoring. Alternatively, if during step 1002, the second recording device does not record any signals that would indicate the presence of low voltage impulses at the stimulation device, then it may be determined that the system is not functioning properly in step 1006. At this point, a troubleshooting process may be used to determine a possible cause for the malfunction in step 1008.

In some embodiments, a paralysis monitoring system may use information from a second recording device to interpret signals received at a first recording device. For example, the information from signals recorded at the second recording device could be used to select, or filter, or otherwise modify, the signals received at the first recording device.

FIG. 13 is a schematic view of a set of electrical signals. Here a first signal 1102 corresponds to an exemplary signal that may be received at a first recording device located over a target muscle region. First signal 1102 signal includes clear response peaks that indicate a response in the muscles to nerve stimulation. A second signal 1104 corresponds to an exemplary signal that may be received at a second recording device located away from the target muscle region. Second signal 1104 includes distinctive waveform regions 1105 that are indicative of low voltage impulses being generated from a nearby source (i.e., a stimulation device). A third signal 1106 corresponds to a filtered signal that is determined using information from first signal 1102 and second signal 1104. As used herein, the term "filtered" simply refers to the using information from one signal to modify another signal. In some cases, filtering could refer to direct subtraction of one signal from another. In other cases, filtering could refer to first transforming the second signal (e.g., translating it by an offset and/or inverting it) and then subtracting it from the first signal. In still other cases, filtering could refer to a more general process whereby information from the second signal is used to modify the first signal.

In some embodiments, filtering the first signal using information about the second signal may act to clean up the first signal. That is, the filtering process could help reduce noise or other information from the signal that is not directly related to signals generated during an evoked muscle response to the stimulating impulses. In some embodiments, the second signal could be used to decide if a particular waveform in the first signal may in fact be a muscle response signal or just noise. That is, the second signal may be used to select for true response signals.

For clarity, the detailed descriptions herein describe certain exemplary embodiments, but the disclosure in this application may be applied to any types of stimulation devices and/or recording devices suitable for providing low voltage stimulation to nerves and recording the muscle response thereto. While various embodiments have been described, the description is intended to be exemplary, rather than limiting and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the appended claims.

What is claimed is:

1. A paralysis monitoring system comprising:
a nerve stimulation device configured to deliver a series of low voltage electrical impulses to a nerve to produce only sub-visible muscle responses, wherein the low voltage electrical impulses are 4 millivolts or less;
a recording device configured to record electrical activity associated with an evoked muscle response caused by the series of low voltage electrical impulses;
wherein the nerve stimulation device is configured to transmit the low voltage electrical impulses to a patient based on a body mass index of the patient;
wherein the nerve stimulation device is configured to transmit the low voltage electrical impulses in the range of about 0.5 millivolts to 1.5 millivolts to patients having a body mass index in a first range; and
wherein the nerve stimulation device is configured to transmit the low voltage electrical impulses in the range of about 1.5 millivolts to 4 millivolts to patients having a body mass index in a second range that is higher than the first range.

2. The paralysis monitoring system according to claim 1, wherein the nerve stimulation device and the recording device are disposed on a strip.

3. The paralysis monitoring system according to claim 1, wherein the recording device comprises an electrode or a needle.

4. The paralysis monitoring system according to claim 1, wherein the nerve stimulation device comprises a transcutaneous electrode probe configured to transmit milliamp current.

5. The paralysis monitoring system according to claim 1, wherein the nerve stimulation device is configured to provide the low voltage electrical impulses on an automatic cycling schedule.

6. The paralysis monitoring system according to claim 5, wherein the automatic cycling schedule transmits the low voltage electrical impulses on an incremental basis from 0.1 millivolts up to 2 millivolts.

7. A method of administering a paralysis drug to a patient, the method comprising:
attaching a nerve stimulation device to a patient's anatomy;
attaching a recording device to the patient's anatomy;
administering a first dose of a paralysis agent to the patient;
transmitting low voltage electrical impulses from the nerve stimulation device to the patient, wherein the low voltage electrical impulses are 4 millivolts or less;
receiving a response signal corresponding to muscle activity of the patient in the recording device;
using information related to the response signal to determine an amount of the paralysis agent to administer as a second dose; and
administering the second dose of the paralysis agent to the patient;
wherein the nerve stimulation device is configured to transmit the low voltage electrical impulses to the patient based on a body mass index of the patient;
wherein the nerve stimulation device is configured to transmit the low voltage electrical impulses in the range of about 0.5 millivolts to 1.5 millivolts to patients having a body mass index in a first range; and
wherein the nerve stimulation device is configured to transmit the low voltage electrical impulses in the range of about 1.5 millivolts to 4 millivolts to patients having a body mass index in a second range that is higher than the first range.

8. The method according to claim 7, wherein the low voltage electrical impulses have magnitudes to produce only sub-visible muscle responses.

9. The method according to claim 7, wherein using information related to the response signal includes comparing the response signal to a baseline recording of the patient's muscle activity.

10. The method according to claim 9, wherein the second dose of the paralysis agent is administered if the response signal is substantially similar to the baseline recording.

11. The method according to claim 7, the method further comprising attaching a second recording device to the patient's anatomy, wherein the second recording device is located away from the first recording device.

12. The method according to claim 11, wherein the method further comprising checking that electrical signals corresponding to the low voltage impulses are recorded at the second recording device.

13. The method according to claim 11, the method further comprising using information from a second response signal recorded at the second recording device to interpret the response signal received at the recording device.

14. The paralysis monitoring system according to claim 6, wherein the low voltage electrical impulses are increased until a predetermined muscle response is received by the recording device.

15. The paralysis monitoring system according to claim 1, wherein the recording device is configured to record a spike focus of the evoked muscle response.

16. The paralysis monitoring system according to claim 1, further comprising an alarm configured to provide an alert upon detecting a return of response signals or muscle activity of a patient.

17. The paralysis monitoring system according to claim 1, wherein the paralysis monitoring system is configured to apply an intermittent pulse that is repeated periodically; and
wherein the paralysis monitoring system is further configured to measure and record a response to the intermittent pulse to determine an effect of a paralytic agent.

18. The paralysis monitoring system according to claim 1, further comprising a signal processor in communication with the recording device.

19. The paralysis monitoring system according to claim 18, wherein the signal processor is connected to a display.

20. A paralysis monitoring system comprising:
a nerve stimulation device configured to deliver a series of low voltage electrical impulses to a nerve of a patient to produce only sub-visible muscle responses, wherein the low voltage electrical impulses are 4 millivolts or less;
a recording device configured to record electrical activity associated with an evoked muscle response of the patient caused by the series of low voltage electrical impulses;
wherein the nerve stimulation device is configured to provide the low voltage electrical impulses on an automatic cycling schedule;

wherein the recording device is configured to confirm paralysis of the patient when the low voltage electrical impulses do not produce an evoked muscle response;

wherein the nerve stimulation device is configured to transmit the low voltage electrical impulses to the patient based on a body mass index of the patient;

wherein the nerve stimulation device is configured to transmit the low voltage electrical impulses in the range of about 0.5 millivolts to 1.5 millivolts to patients having a body mass index in a first range; and wherein the nerve stimulation device is configured to transmit the low voltage electrical impulses in the range of about 1.5 millivolts to 4 millivolts to patients having a body mass index in a second range that is higher than the first range.

* * * * *